United States Patent [19]

Hess et al.

[11] Patent Number: 5,104,898
[45] Date of Patent: Apr. 14, 1992

[54] METHOD OF PREVENTING GRAFT REJECTION IN SOLID ORGAN TRANSPLANTATION

[75] Inventors: Richard A. Hess, Gaithersburg; R. Michael Blaese, Rockville; Christopher D. Stone, Bethesda, all of Md.

[73] Assignee: The United States of America as represented by the Department of Health and Human Services, Washington, D.C.

[21] Appl. No.: 386,114

[22] Filed: Jul. 28, 1989

[51] Int. Cl.$^5$ .............................................. A61K 31/19
[52] U.S. Cl. ................................... 514/557; 514/574; 514/885
[58] Field of Search ........................ 514/557, 574, 885

[56] References Cited

U.S. PATENT DOCUMENTS 4,670,467  6/1987  Hess et al. ............................ 514/557

OTHER PUBLICATIONS

Storb et al., British Journal of Haematology 72 pp. 567–572 (1989).
Tollenmar et al., Transplantation Proceedings 21(1), pp. 3008–3010 (1989).
Santos et al., Bulletin of the Johns Hopkins Hospital 116, pp. 327–340 (1965).
Hectman et al., Surgical Forum 13, pp. 55–57 (1962).
Blumenstock et al., Surgery 51, pp. 541–555 (1962).
Meekee et al., Annals of the New York Academy of Science 87, pp. 203–213 (1960).
Farber, Blood 4, pp. 160–167 (1949).
Vogelsang et al., Transplantation 41, pp. 644–647 (1986).
Vogelsang et al., Marrow Transplantation 3, pp. 393–398 (1988).
Heney et al., Biomed. Pharmacother. 44, pp. 199–204 (1990).
Tamura et al., Transplantation 49, pp. 20–25 (1990).
Emre et al., European Surgical Research 22, pp. 336–339 (1990).
Murphy et al., Journal of Med. Exp. Clin. 1, pp. 66–73 (1970).
Murphy et al., Sth. Afr. Med. J. (spec. suppl.) 42, pp. 26–37 (1968).
Weber et al., Sth Afr. Med. J. (Spec. Suppl.) 42, pp. 37–51 (1968).
Hellmann et al., British Medical Journal 2, pp. 687–689 (1965).
Stites et al., Basic and Clinical Immunology, Lang Medical Publications 1984, pp. 484–487, 771 and 767.
Roitt et al., Immunology C. V. Mosby Co. 1984, pp. 24.1–24.9.

Primary Examiner—Frederick E. Waddell
Assistant Examiner—Zohreh A. Fay
Attorney, Agent, or Firm—John E. Tarcza

[57] ABSTRACT

A method is disclosed for preventing graft rejection of transplanted solid organs, in mammal recipients thereof, by administering an effective graft rejection preventative amount of succinylacetone to said mammals.

20 Claims, No Drawings

METHOD OF PREVENTING GRAFT REJECTION IN SOLID ORGAN TRANSPLANTATION

BACKGROUND OF THE INVENTION

1. FIELD OF THE INVENTION

The present invention relates to methods of preventing graft rejection following solid organ transplantation. More specifically, the invention relates to a method of preventing graft rejection in solid organ transplantation, by administering succinylacetone to recipients of solid organ transplants.

2. DESCRIPTION OF RELATED ART

Succinylacetone (4,6-dioxoheptanoic acid) is an irreversible inhibitor of the second enzyme of the heme biosynthetic pathway, delta-amino levulinic acid dehydrase (ALAD). Initial studies with the compound focused on its ability to inhibit the growth of erythroleukemic cells, through inhibition of heme biosynthesis, but it is also capable of impairing the growth of other tumors by a mechanism independent of heme biosynthesis. Such an activity is disclosed in the article, Tschudy et al, "Growth Inhibitory Activity of Succinylacetones: Studies with Walker 256 Carcinosarcoma" *Oncology* 40:148 (1983), which is hereby incorporated by reference. Notwithstanding succinylacetone's ability to initially inhibit the growth of the Walker 256 tumor, continuous treatment with succinylacetone can actually facilitate allogeneic tumor growth in rats by suppressing the normal immune rejection process.

Succinylacetone is also active in suppressing rat antibody responses to sheep red blood cells in vivo and in inhibiting mitogen and antigen responses by human lymphocytes in vitro. This characteristic of the compound is disclosed in Tschudy et al, "Immuno-suppressive Activity of Succinylacetone" *J. Lab & Clin. Med.*, 99(4):526 (1982), hereby incorporated by reference.

In spite of the potent effects associated with the administration of succinylacetone, one month's treatment with the compound has been shown not to demonstrate significant histopathologic abnormalities in any non-lymphoid organ. Furthermore, there was a 12% decrease in hematocrit and a 20% decrease in hemoglobin with such administration, due to suppression of heme production, this decrease in hemoglobin is only 40% of what would be expected if there had been total inhibition of heme production, ibid.

Succinylacetone has also been successfully used to totally inhibit graft vs host disease (GVHD) in allogeneic bone marrow transplantation. For example, *Journal of Immunology*, 139(9), 2845–2849(1987), disclose succinylacetone to be effective in preventing graft vs host disease, where it is shown that in spite of succinylacetone's strong effects on heme biosynthesis and immune function, succinylacetone does not interfere with engraftment in hematopoietic reconstitution. Furthermore, after one month of treatment, there was only a minor depression of hemoglobin and lymphocytes in the blood and these parameters normalized when the drug was stopped. Further, animals treated with succinylacetone gained weight and no toxicity to other organ systems was seen.

U.S. Pat. No. 4,670,467, issued to Hess et al, hereby incorporated by reference, also discloses a method of controlling graft versus host reaction with succinylacetone.

The effects of succinylacetone on the development of S-antigen-induced experimental autoimmune uveitis (EAU) in rats has been studied and in vivo treatment with succinylacetone has been shown to inhibit in vitro S-antigen-induced lymphocyte proliferative responses in cells from popliteal lymph nodes, as well as decrease S-antigen antibody production, Skolic et al, Clinical Immunology and Immunopathology, 49, 63–71 (1988).

Furthermore, U.S. Pat. application Ser. No. 07/191,067 filed on May 6, 1988, hereby incorporated by reference, is directed to a method of treating autoimmune disease using succinylacetone.

Of the above references, none do any more than simply conjecture that it might be possible to use succinylacetone in solid organ transplantation.

SUMMARY OF THE INVENTION

The failure of major organs is a principal cause of disease and death in mammals. Surgical replacement of a diseased organ, by transplantation with a normal organ obtained from another mammal of the same species, can be a life saving procedure. Unfortunately, normal bodily immune defense mechanisms recognize such solid organ transplants as foreign and attack them, resulting in graft failure and rejection. Transplantation of several organs including kidney, liver, heart, and lungs has been achieved with varying degrees of success by employing techniques to interfere with immune mediated graft rejection. Unfortunately, there is no one single immunosuppressive agent or technique which is useful in all settings involving organ transplantation, and the usefulness of many of the agents in common usage is limited by their toxicity. In some cases, this associated toxicity may actually hinder the normal functioning of the transplant itself.

In view of the above, and more specifically, in view of toxicity drawbacks associated with known immunosuppressants used to prevent graft rejection in solid organ transplants, the present invention provides a method for preventing graft rejection of solid organ transplants, by administering succinylacetone to mammals, including humans, who are recipients of transplanted solid organs.

Specifically, the present invention provides that succinylacetone may be used in:

A method of preventing graft rejection in a mammalian recipient of a solid organ transplant, by administering to said mammalian recipient an effective graft rejection preventative amount of succinylacetone; or a pharmaceutically acceptable salt thereof.

The following glossary of terms is provided in order to remove any vagueness which may exist as to their meanings as used herein.

The term "solid organ" as used herein, means a heart, skin, a liver, a lung, a kidney, a pancreas, or an intestine, endrocrine glands, a bladder, or a skeletal muscle.

The term "pharmaceutically acceptable salt" means alkali metal salts, such as sodium or potassium salts, and alkali earth metal salts, such as calcium salts, of succinylacetone. The sodium salt of succinylacetone may be formed by neutralizing succinylacetone with sodium hydroxide, its preparation should be considered exemplary of the other pharmaceutically acceptable salts of succinylacetone.

DETAILED DESCRIPTION OF THE INVENTION

The immune system operates through a complex interaction of cells and humoral factors. Many compounds and biologicals have been shown to suppress some component of the system. Some immunosuppressives have efficacy in the treatment of human disease whereas others are limited in clinical efficacy because of unacceptable toxic side effects. No one immunosuppressive agent is useful for treatment in all situations. Therefore it is important to develop a variety of immunosuppressive agents which will enlarge the spectrum of disorders which can be successfully treated by immunosuppression. Each of the available agents has significant toxicities which limit their use in some or all patients. For example, Cyclosporin A has profound and irreversible nephrotoxicity. Corticosteroids may inhibit body growth, cause hypertension, or precipate diabetes. Cyclophosphamide and other cytotoxic drugs may be irreversibly toxic to the bone marrow and/or bladder and are associated with the delayed appearance of malignancies.

In view of the above, we herein advantageously provide for the use of succinylacetone in a method of preventing graft rejection in solid organ transplants.

Unlike present immunosuppressant drugs used to prevent graft rejections in solid organ transplantations, succinylacetone appears to have great potential in facilitating solid organ transplantation, while at the same time exhibiting relatively little systemic toxicity.

In short, succinylacetone possesses several characteristics other than low systemic toxicity, which we have found make it advantageous to utilize in the prevention of graft rejection of solid organ transplants. These characteristics include its high water solubility, which can facilitate its delivery as an immunosuppressant drug, and its ability to be synthesized and purified by relatively conventional chemical processes, since it is a simple 7 carbon organic acid.

It is noted, however, that even though succinyl acetone may be easily synthesized, it is also available commercially, for example, Aldrich Chemical Co., Inc., 940 W. Saint Paul Avenue, Milwaukee, Wis. 53233, U.S.A., lists 4,6-dioxoheptanoic acid in its catalogue (1988-1989) as commercially available at a purity of 98%.

The following Experimental Section, is meant to more fully exemplify certain aspects of the present invention disclosed therein. It should not, however, be considered to unduly limit the present invention, since it is fully envisioned that by showing succinylacetone can prevent graft rejection in the instance of heart transplantation, it will be readily understood by those skilled in the art to also prevent graft rejection in the instance of other solid organ transplantations, such as those solid organs included within the definition herein provided. Furthermore, it should be understood that the present invention is only limited by the scope of the claims appended hereto.

Experimental Section

General

We chose heterotopic transplantation of rat hearts as an appropriate scientific model to generally demonstrate succinylacetone's suppression of solid organ transplant rejection. In the model, we utilized the rat strains, ACI and LBN (Lewis x Brown Norway) which are totally disparate at the RT1, RT2 and RT3 loci of the rat MHC (major histocompatibility complex), RT1 being the primary histocompatibility antigen responsible for tissue rejection.

Hearts from ACI donors were placed in the peritoneal cavity of the recipient LBN rats. The anastomosis, donor aorta to recipient aorta, donor pulmonary artery to recipient inferior vena cava, provides perfusion of the heart, which beats in a normal rhythm regulated by its own sinoatrial node. The remaining vessels of the graft heart are tied off. Syngeneic hearts transplanted in this manner may continue to beat for more than one year. Function and condition of a graft heart may be determined by palpating the graft heart in the peritoneal cavity of the recipient. Enlargement, decreased rate and decreased contraction force are indications of graft rejection processes. The presence of the graft heart has minimal effect on cardiopulmonary physiology of the recipient and these animals remained healthy and active throughout the experiment.

Graft hearts which stopped beating were removed and the histology studied to asses general physiology and whether the heart showed signs of rejection, such as a mononuclear cell infiltrate. In this model, hearts which stop functioning prior to day 5, and which show no histological evidence of rejection, are considered technical failures. An example of a technical failure is inadequate perfusion due to the heart twisting on the pedicle.

Materials and Methods

The ACI and LBN rats were supplied by Charles River, Kingston, Pa. Succinylacetone was purchased from Colorado Biotechnology Inc., Casper, Wyo. Alzet osmotic minipumps (model 2ML2 or 2ML4) were obtained from Alza Corp., Palo Alto, Calif.

Recipient LBN rats ranged in weight from 325 to 350 grams. ACI donor weights ranged from 200-250 grams. Succinylacetone was delivered to treated animals as an aqueous solution (pH 6.8-7.2) by osmotic minipumps implanted subcutaneously under light ether anesthesia. Using two pumps per rat and adjusting the concentration of succinylacetone up to 600 mg/ml, dosage of 163 to 260 mg/kg/day were obtained. The treatment period ranged from 12 to 27 days. Control rats received saline via minipumps implanted subcutaneously or by subcutaneous injection. Twenty four to 72 hours after the pumps were implanted, the heterotopic heart transplant was performed. The hearts were transplanted using a modification of the technique of Ono and Lindsey (J. of Thoracic and Cardiovascular Surgery, 57, 225-229 (1969). The rats were palpated daily and asystole defined the day of rejection.

Results

The mean survival time for control grafts in the ACI →LBN model is 6+1 days (mean±standard deviation, n=9). To obtain a significance of P>0.001 survival times greater than 10 days are required for the treated animals. Table 1 shows the survival data for 30 heart allografts.

TABLE I

| Treatment Duration (days) | SA Dosage mg/kg/day | No. of Hearts Transplanted | Results (days post transplant) |
|---|---|---|---|
| control | 0 | 12 | all rejected d-6 + 1 |
| 12 | 241 | 2 | 1 TF* d-5, 1 rej. d-37 |
| 25 | 196 | 2 | 1 rej. d-48, 1 rej. d-58 |
| 24 | 163 | 2 | 1 TF d-3, 1 rej. d-47 |
| 11-13 | 260 | 5 | rej. mean d-31, range d-27-28 |
| 27-28 | 260 | 6 | rej. mean d-46, |

TABLE I-continued

| Treatment Duration (days) | SA Dosage mg/kg/day | No. of Hearts Transplanted | Results (days post transplant) |
|---|---|---|---|
| | | | range d-37-51 |

*TF = technical failure

Discussion of Results

In Table 1, it is shown that those rats receiving succinylacetone had mean survival times longer than those observed for control animals. The results obtained are highly significant ($P > 0.001$) and thus succinylacetone is effective in preventing graft rejection in solid organ transplants.

It is also noted that 13 rats treated with succinylacetone (not in Table 1), for a period of 120-132 days, had functionary graft hearts when they were killed at days 131 and 132, thus further adding to the clinical significance of the treatment.

In addition to the scientific experiment performed above, we have also performed a similar scientific experiment, utilizing succinylacetone to prevent graft rejection when heterotopic transplants of allogenaic hearts were conducted in non-human primates (cynomolgus and rhesus monkeys). In the experiment, favorable results were obtained.

It is also noted that we have performed preliminary testing with succinylacetone to prevent graft rejection in the transplantation of skin in mammals (rats), and that favorable results have also been obtained in such tests.

Pharmaceutical Compositions

In the method provided herein, for preventing graft rejection of solid organ transplants in a mammal, it is fully envisioned that succinylacetone can be administered either orally or by injection, e.g., intravenously or subcutaneously, and that it will be administered daily either in a single bolus dose, or in periodic bolus doses, or by continuous infusion in a pharmaceutical composition comprising succinylacetone and a pharmaceutically acceptable carrier.

For example, succinylacetone may be formulated into preparations for injection by dissolving, suspending or emulsifying the same in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Likewise, in the case of an oral preparation, succinylacetone may be used alone or in combination with appropriate additives to make tablets, powders, granules or capsules, e.g., with conventional additives such as lactose, mannitol, corn starch or potato starch; with binders such as crystalline cellulose, cellulose derivatives, acacia or corn starch; with disintegrators such as corn starch, potato starch or sodium carboxymethylcellulose; with lubricants such as talc or magnesium stearate; and if desired, with diluents, buffering agents, moistening agents, preservatives or flavoring agents.

A suitable dosage of succinylacetone to be administered to prevent graft rejection of a transplanted solid organ in a mammal, is thought to be about 10 to 1,000 mg/kg/day of the free acid, and thought preferably to be about 100 to 300 mg/kg/day of the free acid. Of course, the amount needed to be administered to prevent organ rejection in a patient can vary according to the type and number of organs to be transplanted in a patient, as well as with the age of the patient. Further, it is noted that the appropriate amount of succinylacetone to be administered over a 24 hour period may vary with the mode of administration, i.e., whether the drug is administered as a single bolus dose, in periodic bolus doses, or by continuous infusion. Nonetheless, whatever the type of solid organ transplanted, or dosing schedule used, the amount of succinylacsetone administered must advantageously be an amount sufficient to prevent graft rejection.

In order to administer succinylacetone effectively, it is thought that administration of the compound should be started simultaneously with transplantation of a solid organ into a mammaline species. However, it is not precluded herein that administration of the compound can be started either within the 24 hours preceding transplantation of a solid organ, or within the 24 hours following transplantation of a solid organ. It is also not precluded herein that administration of succinylacetone can be started after the transplantation to replace, or supplement, other compounds being administered to a patient to prevent graft rejection. In the case of a heart transplant, it is thought that the succinylacetone may have to be administered over the remaining lifetime of a patient, in order to control graft rejection processes. However, the present invention should not be considered limited by the same, since other solid organ transplants may not require such lengths of administration.

The present invention is limited only by the scope of the appended claims.

What is claimed is:

1. A method of preventing graft rejection in a mammalian recipient of a transplanted solid organ, by administering to said mammalian recipient an effective graft rejection preventative amount of succinylacetone, or a pharmaceutically acceptable salt thereof.

2. The method of claim 1, wherein said transplanted solid organ is a heart, skin, a lung, a liver, a pancreas, an intestine, an endocrine gland, a bladder, or a skeletal muscle.

3. The method of claim 1, wherein said transplanted solid organ is a heart.

4. The method of claim 2, wherein about 10 to 1000 mg/kg/day of the free acid of succinylacetone or a pharmaceutically acceptable salt thereof is administered to said mammalian recipient.

5. The method of claim 2, wherein about 100 to 300 mg/kg/day of the free acid of succinylacetone or a pharmaceutically acceptable salt thereof is administered to said mammalian recipient.

6. The method of claim 3, wherein about 10 to 1000 mg/kg/day of the free acid of succinylacetone or a pharmaceutically acceptable salt thereof is administered to said mammalian recipient.

7. The method of claim 3, wherein about 100 to 300 mg/kg/day of the free acid of succinylacetone or a. pharmaceutically acceptable salt thereof is administered to said mammalian recipient.

8. The method of claim 2, wherein said mammalian recipient is a primate.

9. The method of claim 3, wherein said mammalian recipient is a primate.

10. The method of claim 1, wherein said mammalian recipient is a human.

11. The method of claim 2, wherein said mammalian recipient is a human.

12. The method of claim 3, wherein said mammalian recipient is a human.

13. The method of claim 4, wherein said mammalian recipient is a human.

14. The method of claim 5, wherein said mammalian recipient is a human.

15. The method of claim 6, wherein said mammalian recipient is a human.

16. The method of claim 7, wherein said mammalian recipient is a human.

17. A method of preventing graft rejection in a mammalian recipient of a heart transplant, which method comprises administration by injection to said mammalian recipient 100–300 mg/kg/day of the free acid of succinylacetone or sodium succinylacetone, in a pharmaceutical composition.

18. The method of claim 17, wherein said mammalian recipient is a primate.

19. The method of claim 18, wherein said mammalian recipient is a human.

20. The method of claim 17, wherein said mammalian recipient is a rat.

* * * * *